United States Patent
Alfini

(10) Patent No.: US 6,894,427 B2
(45) Date of Patent: May 17, 2005

(54) NASAL VIBRATION TRANSDUCER

(75) Inventor: Susan S. Alfini, Dayton, MN (US)

(73) Assignee: Dymedix Corp., Minneapolis, MN (US)

( * ) Notice: Subject to any disclaimer, the term of this patent is extended or adjusted under 35 U.S.C. 154(b) by 404 days.

(21) Appl. No.: 10/178,882

(22) Filed: Jun. 24, 2002

(65) Prior Publication Data

US 2003/0236467 A1 Dec. 25, 2003

(51) Int. Cl.[7] .............................................. H01L 41/113
(52) U.S. Cl. ....................................... 310/338; 310/365
(58) Field of Search ................................ 310/338, 339, 310/365

(56) References Cited

U.S. PATENT DOCUMENTS

| | | | | |
|---|---|---|---|---|
| 4,499,394 A | * | 2/1985 | Koal ........................... 310/330 |
| 4,600,855 A | * | 7/1986 | Strachan ...................... 310/338 |
| 4,814,661 A | * | 3/1989 | Ratzlaff et al. .............. 310/328 |
| 4,823,802 A | * | 4/1989 | Romanovskaya ........... 600/501 |
| 4,895,160 A | * | 1/1990 | Reents ......................... 600/484 |
| 5,099,702 A | * | 3/1992 | French ...................... 73/862.68 |
| 5,311,875 A | * | 5/1994 | Stasz ........................... 600/537 |
| 5,515,738 A | * | 5/1996 | Tamori ..................... 73/862.46 |
| 5,825,119 A | * | 10/1998 | Shibata et al. .............. 310/338 |
| 5,827,198 A | * | 10/1998 | Kassal ......................... 600/528 |
| D410,584 S | | 6/1999 | Stasz et al. .................. D10/57 |
| D417,161 S | | 11/1999 | Stasz et al. .................. D10/57 |
| 5,996,418 A | * | 12/1999 | Rector et al. ................. 73/702 |
| 6,254,545 B1 | | 7/2001 | Stasz et al. ................. 600/529 |
| 6,383,143 B1 | * | 5/2002 | Rost ............................ 600/534 |
| 6,551,256 B1 | * | 4/2003 | Stasz et al. ................. 600/586 |
| 2004/0039419 A1 | * | 2/2004 | Stickney et al. ............... 607/5 |

FOREIGN PATENT DOCUMENTS

WO  WO 99/34864  *  7/1999  ............ A61N/5/00

* cited by examiner

*Primary Examiner*—Thomas M. Dougherty
(74) *Attorney, Agent, or Firm*—Thomas J. Nikolai; Nikolai & Mersereau, P.A.

(57) ABSTRACT

A vibration transducer specially configured for attachment to a subject's nose for producing an electrical output signal relating to a subject's snoring pattern. The transducer is shaped so as to have a rectangular portion for bridging the dorsum at least one polygonal pad area adapted to be adhesively secured to the ala nasi. The transducer is a laminated arrangement incorporating a polyvinylidene fluoride film exhibiting piezoelectric properties.

8 Claims, 6 Drawing Sheets

NASAL VIBRATION TRANSDUCER

BACKGROUND OF THE INVENTION

I. Field of the Invention

This invention relates generally to electronic transducers for use in monitoring snoring episodes during sleep studies, and more particularly to a transducer especially designed to be worn on the nose for producing an electrical output proportional to vibration of selected portions of the nose as snoring takes place.

II. Discussion of the Prior Art

In U.S. Pat. No. 5,311,875 to Stasz, which is hereby incorporated by reference, there is described a system for electronically monitoring breathing patterns. The system included a transducer, the active element of which comprises a film of polyvinylidene fluoride (PVDF). As those skilled in the art appreciate, this material exhibits both pyroelectric and piezoelectric properties.

In accordance with the Stasz '875 patent, the transducer was adapted to be mounted on the upper lip of a subject where it would be exposed not only to vibration resulting from snoring but also thermal differences due to respiratory air flow during nasal breathing. The piezoelectric properties of the PVDF film produces a signal proportional to vibration and the pyroelectric properties produces a signal proportional to temperature fluctuations. In a subsequent Stasz et al. U.S. Pat. No. 6,254,545, there is described a combination thermal and vibration sensor for use in sleep monitor equipment where, again, a thin film of PVDF material is the active element. The PVDF film layer is sandwiched between an outer adhesive tape layer and an inner double-sided layer of adhesive tape. The transducer was particularly shaped for placement on the upper lip such that air entering and leaving the nostrils would impinge upon the transducer and so that a further portion is suspended from the upper lip but overhangs the mouth. The contents of the Stasz '545 patent are also hereby incorporated by reference as if set forth in full herein.

U.S. patent application Ser. No. 09/634,148, filed Aug. 8, 2002, which is assigned to the assignee of the present application, describes a vibration transducer based upon PVDF technology where the transducer comprises a generally rectangular patch that is adapted for placement on a subject's throat for the purpose of picking up vibrations caused by snoring.

Experience has shown that while each of the above-described transducer designs successfully operates for its intended purpose, each has its own type of defect that some patients find objectionable. In particular, the Stasz '875 patent and the Stasz et al. '545 patent are designed to be adhesively adhered to a patient's upper lip. If the person that is the subject of a sleep study has a moustache, it becomes somewhat difficult to adhesively affix the transducer to the upper lip and the moustache prevents more intimate contact with the skin of the lip such that vibrations produced by snoring are greatly attenuated. Moreover, subjects have complained about an objectionable tickling response when the transducer is affixed to the upper lip. The transducer that is the subject of pending U.S. application Ser. No. 09/634, 148 must be placed at a so-called "sweet spot" on the neck, which is sometimes difficult to locate. In locating it, the subject is asked to hum and while doing so, the technician at the sleep lab must feel about the subject's throat to find the location where the vibration resulting from the hum is a maximum.

It is accordingly a principal object of the present invention to provide a vibration transducer that obviates the drawbacks mentioned above while still providing a robust electrical output signal during episodes of snoring so that information relating to snoring patterns can be discerned.

SUMMARY OF THE INVENTION

In accordance with this invention, there is provided a thin, flexible, laminated vibration transducer that is adapted for placement on a subject's nose for producing an electrical signal related to snoring episodes. The transducer comprises an outer layer of adhesive tape having adhesive on one major surface thereof. An intermediate layer of a flexible, conformable plastic film exhibiting piezoelectric properties and having a pattern of metallization on opposed major surfaces thereof is adhered to the outer layer of adhesive tape. First and second elongated conductors or wires, each having an electrode at one end and an electrical connector at another end are arranged such that the electrode on the first conductor is held in contact with the pattern of metallization on one of the opposed major surfaces of the layer of plastic film by the outer layer of adhesive tape and the electrode on the one end of the second conductor is held in contact with the pattern of metallization on the opposite side of the film layer using an inner layer of adhesive tape that has adhesive on each of its opposed major surfaces. The outer and inner layers of adhesive tape have a generally rectangular portion for spanning the dorsum of the nose and at least one integrally attached pad portion for attachment to an ala nasi.

It has been determined that the vibration of the ala nasi during snoring is readily detected by a PVDF transducer.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENTS

Figure 1:
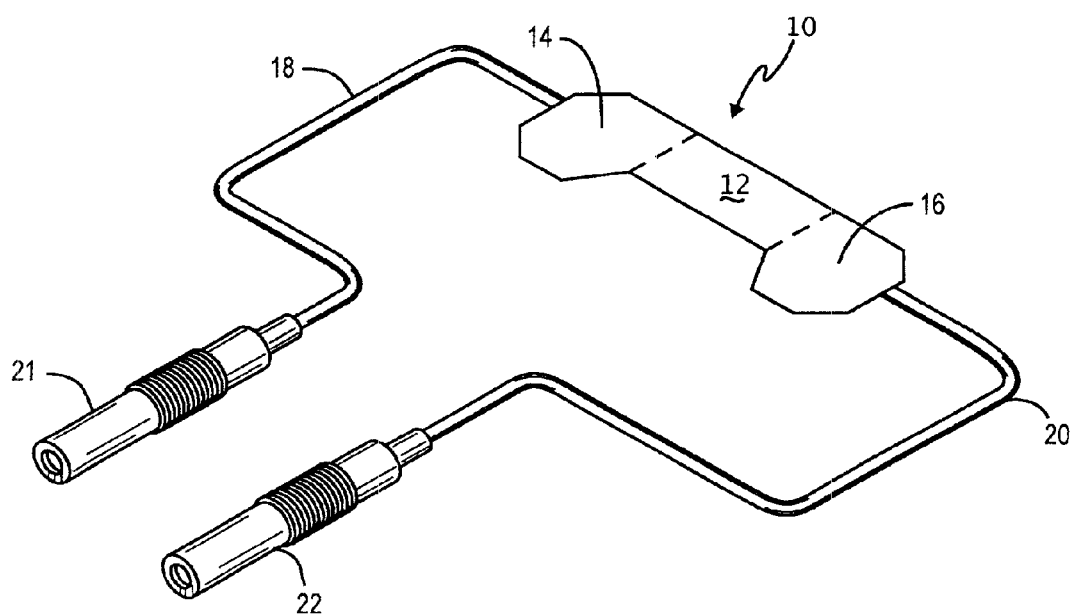
FIG. 1 is a perspective view of a first embodiment of the invention.

Certain terminology will be used in the following description for convenience in reference only and will not be limiting. The words "upwardly", "downwardly", "rightwardly" and "leftwardly" will refer to directions in the drawings to which reference is made. The words "inwardly" and "outwardly" will refer to directions toward and away from, respectively, the geometric center of the device and associated parts thereof. Said terminology will include the words above specifically mentioned, derivatives thereof and words of similar import.

Referring first to FIG. 1, there is indicated generally by numeral 10 a nasal vibration sensor in accordance with the present invention. It comprises a generally rectangular portion 12 with integrally attached polygonal pad portions 14 and 16 on opposed ends of the central rectangular portion. The pad portions may be polygonal in shape, as illustrated, or they may be somewhat rounder or oval in shape. Exiting opposed ends of the transducer are electrical conductors or wires 18 and 20 which lead to connectors 21 and 22 that are adapted to mate with input terminals of an amplifying and signal processing circuit (not shown).

Figure 2:
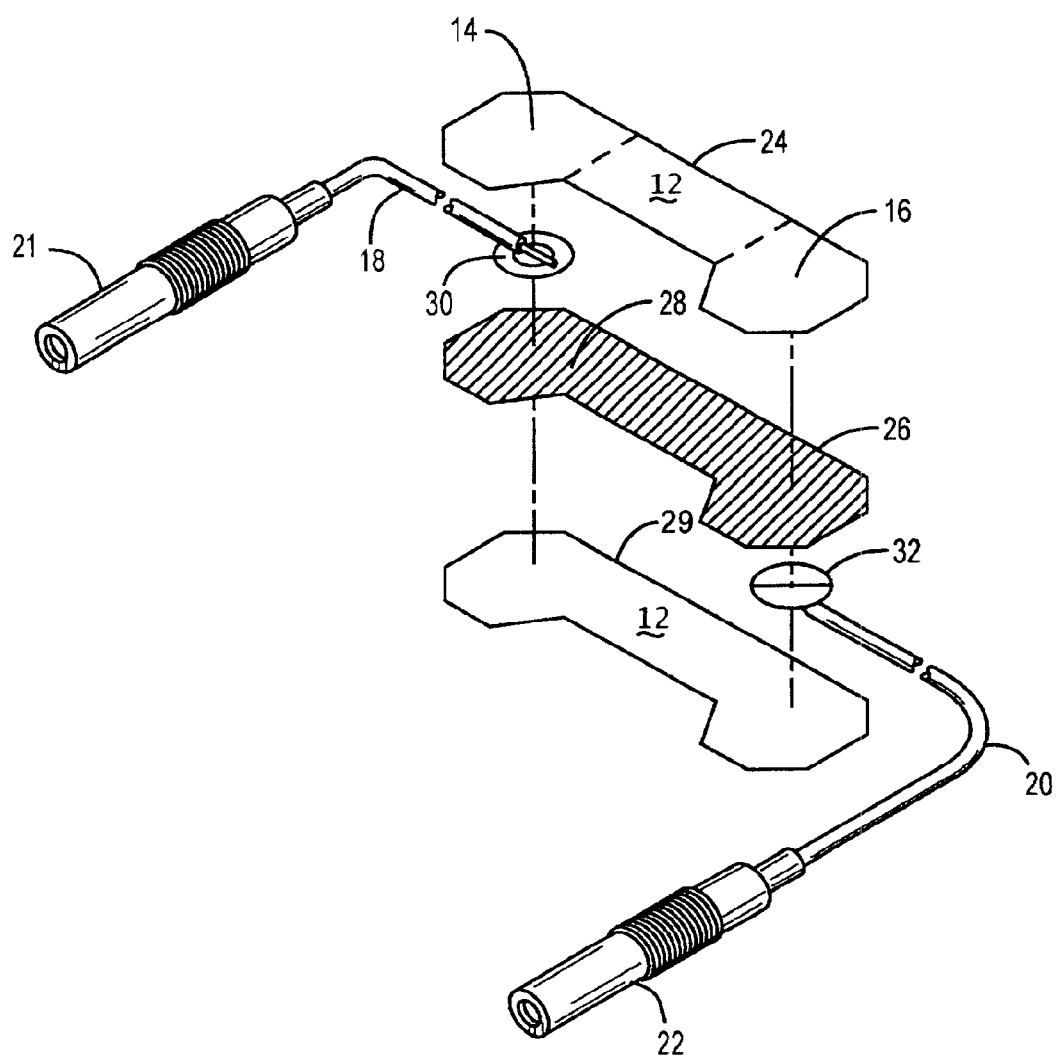
FIG. 2 is an exploded view of the embodiment of FIG. 1.

Referring next to FIG. 2, the exploded view shows that the transducer is of a laminated construction, having an outer layer 24 of adhesive tape, an intermediate layer of polyvinylidene fluoride (PVDF) film 26 and an inner layer 28 of double-sided adhesive tape with an adhesive layer on opposed major surfaces thereof.

The PVDF film 26 has a layer of metallization 28 on opposed major surfaces thereof. The metallization is represented in FIG. 2 by the cross-hatching on the PVDF film layer 26. It is coextensive with the outer layer 24 in terms of area.

With continued reference to FIG. 2, it will be seen that on the end of the conductor or wire 18 is an electrode member 30 and on the end of the wire 20 opposite from the connector 22 is a similar electrode member 32. In its laminated condition, the electrode 30 is held in contact with the layer of metallization 28 on the upper surface of the film layer 26 while electrode 32 engages the pattern of metallization on the undersurface of the layer 26.

Figure 3:
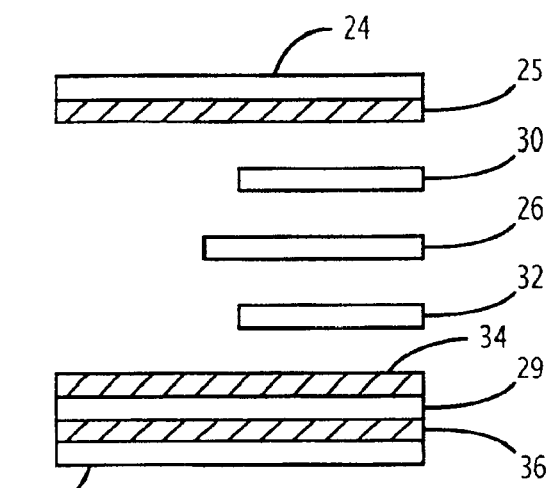
FIG. 3 is an exploded sectional view of the embodiment of FIG. 1.

Referring now to FIG. 3, which is an exploded cross-sectional view taken through the transducer 10, it will be seen that there is an adhesive layer 25 on the undersurface of the tape substrate 24. Likewise, the tape substrate 29 has an adhesive layer 34 on its upper surface and at an adhesive layer 36 on its lower or undersurface. To protect the adhesive layer 36 from contamination prior to use, a release liner 38, which is relatively unaggressively adhered to the adhesive layer 36 is provided. The adhesive layer 36 on the underside of tape substrate 29 is selected so as to be comfortably removable from a subject's skin, yet adherent enough so as to maintain the transducer in place for a period of several hours.

Once laminated, the adhesive layer 25 bonds to the adhesive layer 34 sandwiching the electrode 30, the PVDF film layer 26 and the electrode 32 therebetween. Without limitation, the rectangular portion 12 may be in a range of 3 cm to 5 cm long and 7 mm wide. The pads 14 and 16 may have an area of about 2.25 t0 3 sq. cm.

Figure 4:
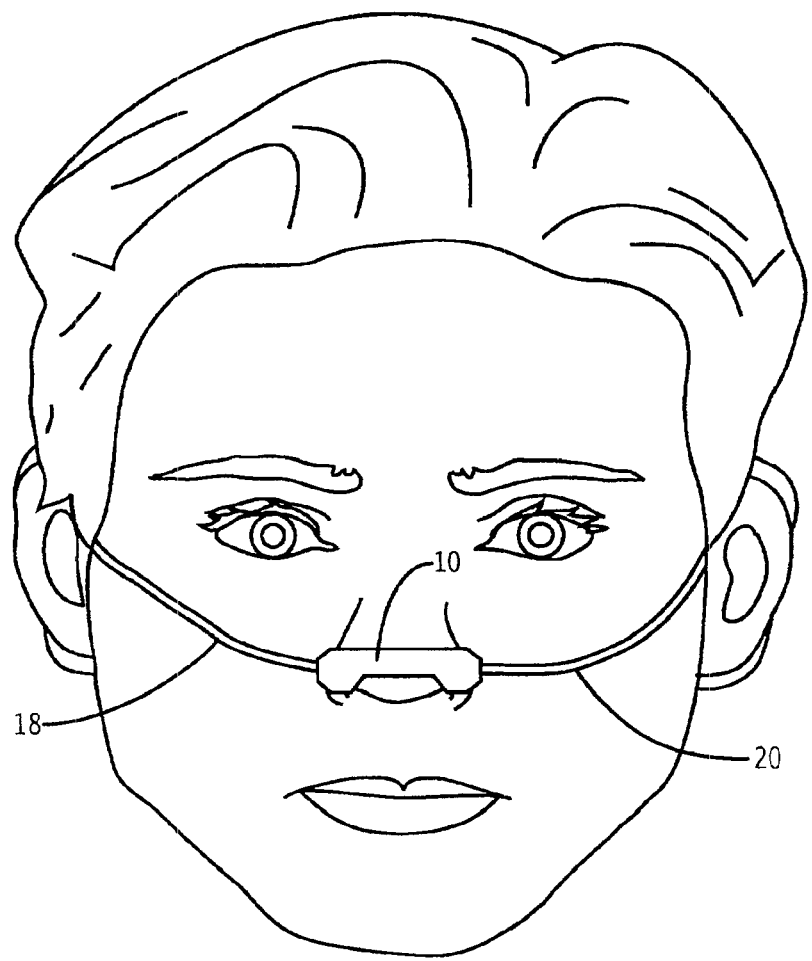
FIG. 4 shows the embodiment of FIG. 1 in place on the nose of a subject.

Referring now to FIG. 4, in use, the release liner 38 is peeled free from the adhesive layer 36 and the rectangular portion 12 of the laminated transducer is placed across the dorsum of the subject's nose and with the pad areas 14 and 16 being adhesively adhered to the ala nasi. The wires 18 and 20 pass over the subject's cheeks and behind the ears where a connection is made between the connectors 21 and 22 and an electronics module (not shown) for receiving and processing signals derived from the transducer 10. It is found that when a person snores, the ala nasi vibrate and those vibrations are picked up by the PVDF film transducer and converted to an electrical signal proportional to the detected vibration signal.

Alternative Embodiment

Figure 5:
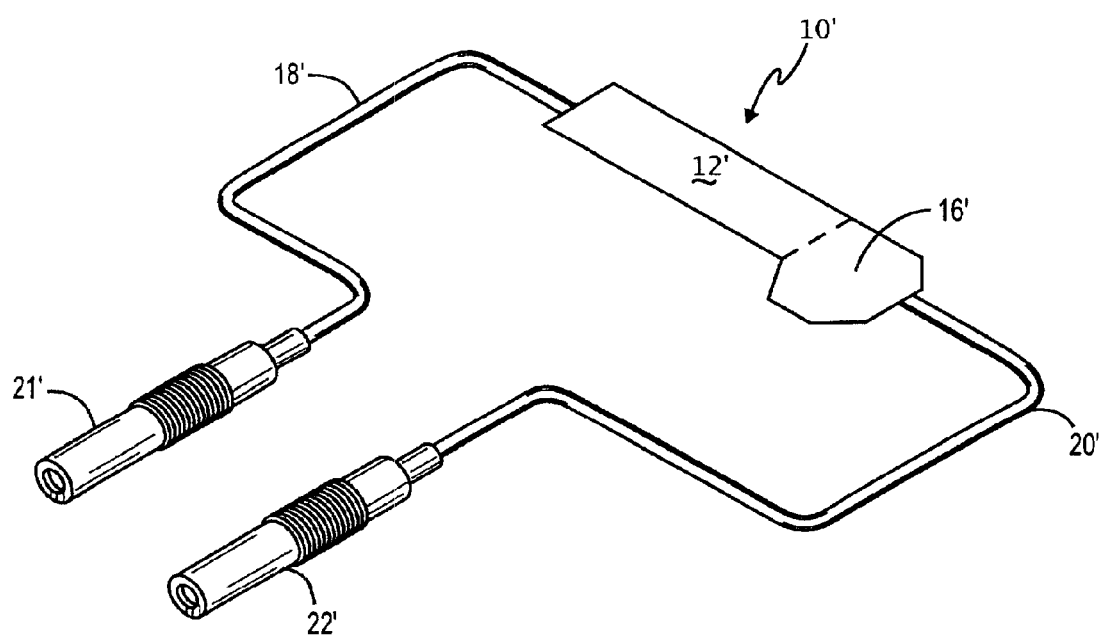
FIG. 5 is a perspective view of an alternative embodiment of the invention.
Figure 6:
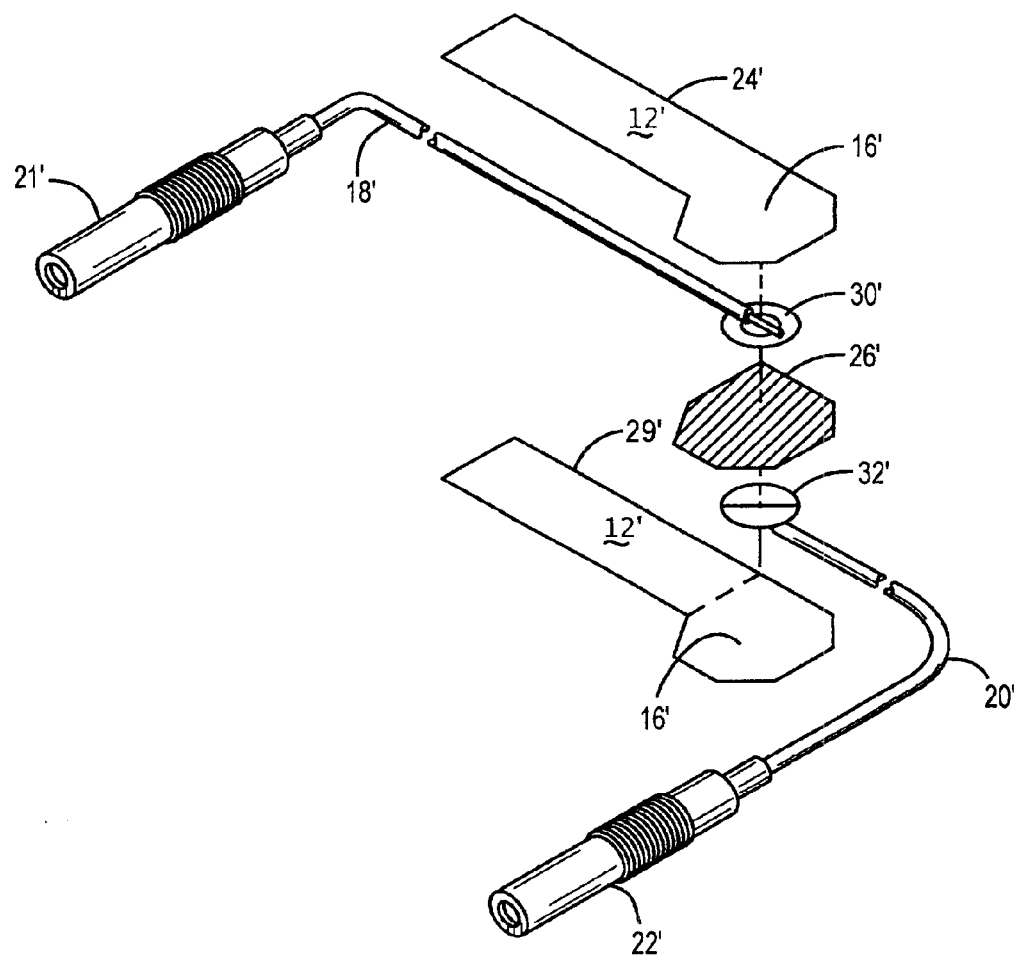
FIG. 6 is an exploded view of the embodiment of FIG. 5.
Figure 7:
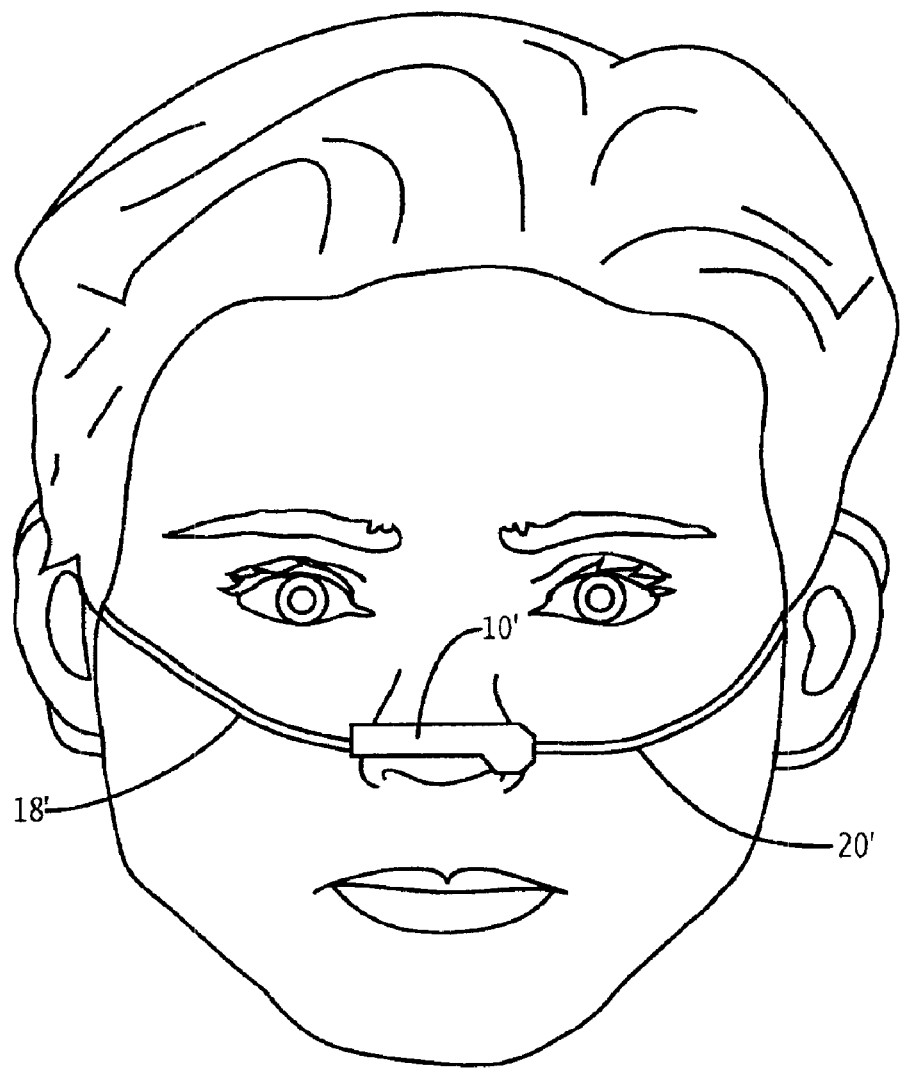
FIG. 7 is a view illustrating the embodiment of FIG. 5 affixed to the nose of a subject.

Referring to FIGS. 5–7, the alternative embodiment differs from the previously described embodiment in only two respects. First, only one pad 16' is integrally attached to one end of the rectangular portion 12' of the transducer and the PVDF film layer 26' is coextensive with the pad area of the outer layer of adhesive tape 24'.

When the transducer 10' is laminated, the adhesive on the undersurface of the outer adhesive tape layer 24' holds the electrode 30' to the upper surface of the PVDF film layer 26'. Likewise, the adhesive layer on the upper surface of the tape 29' adheres the electrode 32' to the pattern of metallization on the undersurface of the PVDF film layer 26'. Furthermore, the adhesive on the undersurface of the outer tape layer 24' bonds to the adhesive on the upper surface of the inner adhesive tape layer 29' except where the film layer 26' is interposed. A release liner is also adhered to the under surface of the inner layer 29' to protect the adhesive on that surface prior to its being used to adhere the transducer device to the nose of a subject.

FIG. 7 shows the alternative embodiment of FIGS. 5 and 6 affixed to a subject. Here, the release layer has been removed and the adhesive on the under surface of the layer 29' attaches the transducer of the subject's nose such that the rectangular portion 12' of the transducer overlays the dorsum and the pad area 16' is bonded to the ala nasi on only one side of the side.

The choice of using a transducer as in FIG. 4 or as in FIG. 7 can depend on the type of data recorder that may be available in a sleep lab. If higher amplitude input signals are required, the transducer of FIG. 4 would be the choice. The transducer of FIG. 4 also offers an advantage of added security in the event one pad area should come loose. The sensor of FIG. 7 offers a lower cost alternative.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A thin, flexible, laminated, vibration transducer adapted for placement on a subject's nose for producing an electrical signal related to snoring episodes, the laminated transducer comprising:
   (a) an outer layer of adhesive tape having adhesive on one major surface thereof;
   (b) an intermediate layer of a flexible, conformable plastic film exhibiting piezoelectric properties and having a pattern of metallization on opposed major surfaces thereof, the intermediate layer being co-extensive with at least a predetermined portion of the outer layer;
   (c) first and second elongated conductors, each having an electrode at one end and an electrical connector at an opposite end, the electrode on the first conductor held in contact with the pattern of metallization on one of the opposed major surfaces of the layer of plastic film by the outer layer of adhesive tape;
   (d) an inner layer of adhesive tape having adhesive on each opposed major surfaces thereof, the electrode on the second conductor held in contact with the pattern of metallization on another of the major surfaces of the layer of plastic film by the adhesive on one major surface of the inner layer of adhesive tape; and
   (e) the outer and inner layers having a generally rectangular portion adapted to span a dorsum of the nose of the subject and an integrally attached pad portion for placement on a ala nasi.

2. The vibration transducer as in claim 1 wherein the outer and inner layers have a generally rectangular portion for spanning a dorsum of the nose of the subject and an integrally attached pad portion on each end of the rectangular portion for placement on each ala nasi of the subject's nose.

3. The vibration transducer of claim 1 and further including:
   (a) a layer of release paper adhered to the adhesive on another major surface of the inner layer of adhesive tape.

4. The vibration transducer of claim 2 and further including:
   (a) a layer of release paper adhered to the adhesive on another major surface of the inner layer of adhesive tape.

5. The vibration transducer of claim 2 wherein the intermediate layer has the same shape configuration as the outer and inner layers.

6. The vibration transducer of any one of claims 1–5 wherein the plastic film is polyvinylidene fluoride.

7. The vibration transducer as in claim 1 wherein the predetermined portion of the outer layer with which the inner layer is coextensive is the pad portion.

8. The vibration transducer as in claim 2 wherein the predetermined portion of the outer layer with which the intermediate layer is coextensive comprise the rectangular portion and the pad portions on each end of the rectangular portion.

* * * * *